United States Patent
Kim et al.

(10) Patent No.: US 9,198,945 B2
(45) Date of Patent: Dec. 1, 2015

(54) COSMETIC COMPOSITOIN CONTAINING A RUBUS COREANUS EXTRACT FOR DIMINISHING SKIN WRINKLES

(71) Applicant: AMOREPACIFIC CORPORATION, Seoul (KR)

(72) Inventors: Dong Hyun Kim, Suwon-si (KR); Jun Seong Park, Suwon-si (KR); Sun Hye Yu, Seongnam-si (KR); Dae Hyuk Kweon, Suwon-si (KR); Hyun Ju Koh, Anyang-si (KR); Won Seok Park, Seoul (KR); Duck Hee Kim, Seoul (KR); Han Kon Kim, Suwon-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 58 days.

(21) Appl. No.: 13/778,176

(22) Filed: Feb. 27, 2013

(65) Prior Publication Data
US 2013/0171282 A1    Jul. 4, 2013

Related U.S. Application Data

(62) Division of application No. 13/381,784, filed as application No. PCT/KR2010/004144 on Jun. 25, 2010, now abandoned.

(30) Foreign Application Priority Data

Jun. 25, 2009 (KR) .................. 10-2009-0058901

(51) Int. Cl.
- A61K 36/73 (2006.01)
- A61K 8/97 (2006.01)
- A61Q 19/08 (2006.01)

(52) U.S. Cl.
CPC . *A61K 36/73* (2013.01); *A61K 8/97* (2013.01); *A61Q 19/08* (2013.01)

(58) Field of Classification Search
None
See application file for complete search history.

(56) References Cited

U.S. PATENT DOCUMENTS

2003/0152545 A1    8/2003    Park

FOREIGN PATENT DOCUMENTS

| CN | 1579366 A | | 2/2005 |
| JP | 2002241299 A | * | 8/2002 |
| KR | 10-2007-0044280 | | 4/2007 |
| KR | 10-2008-0008491 | | 1/2008 |
| KR | 2008008491 A | * | 1/2008 |

OTHER PUBLICATIONS

English translation of KR 2008008491 A to Choi et al. Date: Jan. 2008.*
English translation of First Notification of Office Action and Office Action in CN 201080029147.3 issued Oct. 17, 2012.
Letter from Chinese agent forwarding Office Action dated Nov. 14, 2012.
Foreign language International Search Report for PCT/KR2010/004144 mailed Mar. 31, 2011.
Written Opinion of the International Searching Authority mailed Mar. 31, 2011.

* cited by examiner

*Primary Examiner* — Amy L Clark
(74) *Attorney, Agent, or Firm* — Nixon & Vanderhye P.C.

(57) ABSTRACT

The present invention relates to a cosmetic composition containing a *Rubus coreanus* extract as an active ingredient, and more particularly to a cosmetic composition containing an extract from *Rubus coreanus* processed by traditional oriental medicinal processing technology, in which the *Rubus coreanus* extract has an excellent effect of reducing skin wrinkles by inhibiting the formation of SNARE complexes and the release of a neurotransmitter. The cosmetic composition has excellent stability in formulations compared to conventional products for reducing skin wrinkles and exhibit effects similar to Botox which has been used to reduce skin wrinkles, thereby greatly reducing skin wrinkles without causing adverse effects.

4 Claims, 1 Drawing Sheet

COSMETIC COMPOSITOIN CONTAINING A RUBUS COREANUS EXTRACT FOR DIMINISHING SKIN WRINKLES

This application is a divisional of application Ser. No. 13/381,784 filed Dec. 30, 2011, which in is a U.S. national phase of International Application No. PCT/KR2010/004144 filed 25 Jun. 2010 which designated the U.S. and claims priority to KR 10-2009-0058901 filed 30 Jun. 2009, the entire contents of each of which are hereby incorporated by reference.

TECHNICAL FIELD

The present invention relates to a cosmetic composition containing a *Rubus coreanus* extract as an active ingredient, and more particularly to a cosmetic composition containing an extract from *Rubus coreanus* processed by traditional oriental medicinal processing technology, in which the *Rubus coreanus* extract has an excellent effect of reducing skin wrinkles by inhibiting the formation of SNARE complexes and the release of a neurotransmitter. The cosmetic composition has excellent stability in formulations compared to conventional products for reducing skin wrinkles and exhibit effects similar to Botox which has been used to reduce skin wrinkles, thereby greatly reducing skin wrinkles without causing adverse effects.

BACKGROUND ART

Generally, for the release of a neurotransmitter, a synaptic vesicle containing the neurotransmitter is required to be fused with a presynaptic membrane so that a passage between two boundaries can be formed. Herein, a fundamental force for such membrane fusion is provided by SNARE complexes comprising three kinds of proteins. Particularly, when a release passage of a neurotransmitter is generated by membrane fusion between a synaptic vesicle and a presynaptic membrane, a t-SNARE complex (a complex of a syntaxin-1a protein, and a SNAP-25 protein) attached to a target membrane forms a parallel coiled with a v-SNARE attached to a vesicle. Such SNARE proteins are twisted in a spiral shape. In the membrane fusion, rearrangement of a lipid bilayer, which is widely known in the art, occurs. Since biomembranes strongly repel against each other, the membranes cannot be automatically merged, and thus a strong external force is required to overcome the repulsive force between the membranes. Herein, SNARE proteins generate such a strong force enough to overcome the repulsive force between the membranes. In other words, the formation of a SNARE complex is a force generator to overcome a repulsive power between membranes, and a main action in exocytosis including release of a neurotransmitter. Meanwhile, a neuromuscular junction in the upper layer of muscles acts to regulate the relaxation and constriction of muscles, and the nerve terminal is filled with synaptic vesicles. BoNT (Botulinum neurotoxin; hereinafter referred to as "Botox") is a protease for cleavage of a SNARE protein, which is a main protein involved in the release of a neurotransmitter. Botox cleaves a SNARE protein to block neurotransmission, which results in paralysis of Botox-penetrated muscle cells. Botox irreversibly cleaves the SNARE protein to blocks neurotransmission, whereas so-called "applicable Botox" is a kind of competitive inhibitor that inhibits the formation of a SNARE complex to interfere with neurotransmission. Argireline that is the main component of an applicable botox product currently has disadvantages in that its effect is not reliable, its price is unfavorable due to the characteristics of the synthetic peptide and it is not consumer-friendly.

Developing a neurotransmission inhibitor based on a natural extract can provide a raw material that is significantly inexpensive compared to a peptide material, and a final product produced from the natural extract is consumer-friendly. Thus, the natural extract is easily industrially applied compared to peptide materials.

Meanwhile, a medicinal herb processing technique that is a traditional oriental medicine manufacturing technique is called "Po-je", "Hap-hwa", "Hap-yak", "Su-chi", "Po-ja", "Beob-je" and "Su-sa" in Korean. This technique can be defined as a medicine manufacturing technique of changing the inherent properties of medicinal herbs by processing the medicinal herbs on the basis of the oriental medicine theory.

The processing of medicinal herbs includes selection of correct medicine, removal of impurities, purification, heating, processing employing aids, etc. In some cases, medicinal herbs are processed together with aids suitable for medical applications in order to achieve the administration of medicine according to disease. Because various aids are used in the processing of medicinal herbs, they have different properties and effects, and thus the processed medicinal herbs show different effects. Aids which are currently used in the processing of medicinal herbs are various and broadly divided into liquid aids and solid aids. The liquid aids include liquor, vinegar, brine, honey, ginger juice, licorice juice, black bean juice, saline solution, rice water, horse oil, milk, children urine, and lime water. The solid aids include rice, wheat bran, alum, bean-curd, soil, seashell powder, and sand.

The processing medicinal herbs is carried out to clarify medicines, facilitate the storage of medicines, reduce or remove the toxicity or side effects of medicines, change the properties of medicines to make the medicines more effective, enhance the therapeutic effects of medicines, and the offensive odor and taste of medicines to facilitate the intake of the medicines.

Skin wrinkles are the most noticeable sign of skin aging which occurs due to intrinsic factors, such as aging and stress, or external environmental factors such as air pollution and UV radiation. Wrinkles occur on facial areas, such as the forehead, eye rims, eyebrow, and peri-oral areas, and various portions of the body, such as a neck, neck circumferences, elbows, armpits, hands, and feet. Wrinkles generally start to become visible after about 30 years old, and the number or depth thereof increase with aging. Such wrinkles are considered to occur mainly because reactive oxygen species produced in skin tissues by a skin aging crosslink collagen fibers and elastic fibers forming the majority of the skin dermis to change the production and degradation of such fibers. Antioxidants such as vitamin E, beta-carotene, vitamin C and glutathione, which are used to inhibit skin aging, radical scavengers, or substances such as vitamin A, which increase the synthesis of dermal collagen, have been used to reduce skin wrinkles. However, such cosmetic active ingredients have disadvantages in that they are mostly strongly irritating to the skin or are unstable in formulations to cause discoloration, bad smell and precipitation, and the inherent activity thereof decreases.

Recently, in order to reduce skin irritation of various chemicals, various cosmetics based on natural materials have been developed. Such natural materials have reduced adverse effects on the skin and also have high consumer preference, and thus their value as cosmetic materials is gradually increasing.

Technical Problem

Accordingly, the present inventors have conducted studies on natural materials having an excellent effect of reducing skin wrinkles and, as a result, have found that a cosmetic composition comprising a *Rubus coreanus* extract have an excellent effect of reducing skin wrinkles, thereby completing the present invention.

It is, therefore, an object of the present invention to provide a cosmetic composition containing a *Rubus coreanus* extract as an active ingredient.

Technical Solution

To achieve the above object, the present invention provides a cosmetic composition containing a *Rubus coreanus* extract as an active ingredient.

Advantageous Effects

The cosmetic composition according to the present invention contains as an active ingredient a *Rubus coreanus* extract which inhibits the formation of a SNARE complex and prevents the release of a neurotransmitter, thereby exhibiting an excellent effect of reducing skin wrinkles. Also, because the cosmetic composition of the present invention contains the natural material, it has reduced adverse effects on the skin and has reduced skin irritation. In addition, it has high stability in formulations compared to conventional agents for reducing skin wrinkles, and shows effects similar to Botox which has been used to reduce wrinkles, thereby significantly reducing skin wrinkles without causing adverse effects.

BEST MODE

Figure 1:
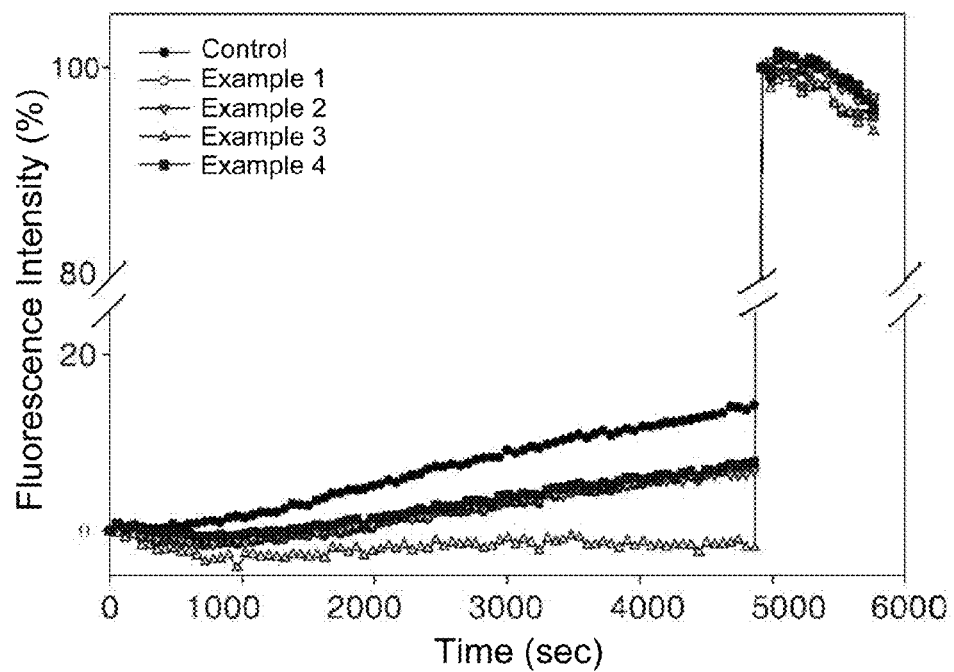
FIG. 1 is a graphic diagram showing the inhibitory effect of a *Rubus coreanus* extract according to the present invention on the membrane fusion phenomenon.

The present invention provides a composition for reducing skin wrinkles which contains a *Rubus coreanus* extract as an active ingredient.

Hereinafter, the present invention will be described in detail.

*Rubus coreanus* that is used in the present invention is the fruit of *Rubus coreanus Miguel* and is odorless, sour and sweet in taste, and warm in nature. *Rubus coreanus* increases renal function and is thus used against involuntary ejaculation, wet dreams and enuresis. It also makes the body light and makes the hair black. It assists in pregnancy and makes the skin soft and beautiful. It was reported to have pharmacological activities, including anti-inflammatory, antioxidant effects and anti-*Helicobacter pylori* activities.

The *Rubus coreanus* extract of the present invention inhibits the formation of a SNARE (soluble N-ethylmaleimide-sensitive factor attachment protein receptor) complex and the release of a neurotransmitter, thereby exhibiting an excellent of reducing skin wrinkles. It can show effects similar to Botox which has been used to reduce skin wrinkles, thereby significantly reducing skin wrinkles without causing adverse effects.

In order to prepare the *Rubus coreanus* extract according to the present invention, *Rubus coreanus* may be processed before extraction with a solvent. Dried *Rubus coreanus* is processed by a boiling process, a steaming process, a roasting process, a baking process, or a combination of two or more thereof. Specifically, *Rubus coreanus* is processed at 60~100° C. for 30 minutes to 2 hours for boiling, 120~150° C. for 3-6 hours for steaming, 100~180° C. for 10 minutes to 1 hour for roasting, and 80~100° C. for 10 minutes to 1 hour for baking. If the processing temperature and time are out of these ranges, the effect of processing *Rubus coreanus* will be insufficient or the components of *Rubus coreanus* can change.

Also, *Rubus coreanus* may be processed together with an aid. Examples of an aid that may be used in the present invention include liquor, vinegar, brine, honey, ginger juice, licorice juice, black bean juice, saline solution, rice water, horse oil, milk, children urine, lime water, rice, wheat bran, alum, bean-curd, soil, seashell powder, and sand.

In the present invention, extraction of *Rubus coreanus* may be carried out by any conventional method known in the art. For example, a *Rubus coreanus* can be obtained by extracting the processed *Rubus coreanus* with water or an organic solvent under reflux, dipping the extract, filtering the dipped solution through filter cloth, centrifuging the filtered solution into residue and a filtrate, and concentrating the separated filtrate under reduced pressure.

Examples of an organic solvent that may be used in the present invention include ethanol, methanol, butanol, ether, ethyl acetate, chloroform, and a mixed solvent of at least one thereof with water. Preferably, 80% ethanol is used. The extraction process is preferably carried out at a temperature of 10~80° C. for 6-24 hours. If the extraction temperature and time are out of these ranges, the efficiency of extraction will be insufficient or the components of *Rubus coreanus* can change.

After the extract has been obtained using the solvent, it may be macerated at room temperature, heated and filtered, according to a conventional method in the art, thus obtaining a liquid material. Alternatively, it may be evaporated to remove the solvent or may be spray-dried or freeze-dried.

The cosmetic composition according to the present invention contains the *Rubus coreanus* extract in an amount of 0.0001-30 wt % based on the total weight of the composition. If the content of the *Rubus coreanus* extract is less than 0.0001 wt %, the effect of reducing skin wrinkles cannot be obtained, and if it is more than 30 wt %, an increase in the content will not lead to a significant increase in the effect thereof.

The cosmetic composition according to the present invention may be formulated into, but not limited to, skin lotion, astringent lotion, milk lotion, nourishing cream, massage cream, essence, pack, foundation, lipstick or powder foundation.

Components other than the extract in the cosmetic composition of the present invention can be suitably selected without difficulty by a person skilled in the art depending on the formulation or intended use of the cosmetic composition.

MODE FOR INVENTION

Hereinafter, the present invention will be described in further detail with reference to examples and test examples. It is to be understood, however, that these examples are for illustrative purposes only and are not to be construed to limit the scope of the present invention.

EXAMPLE 1

Preparation of Extract of Raw Rubus coreanus 1 kg of dried *Rubus coreanus* was added to 5 l of 80% ethanol aqueous solution, extracted three times under reflux, and then dipped at 15° C. for 1 day. Next, the dipped solution was filtered through filter cloth and centrifuged into residue and a filtrate, and the separated filtrate was concentrated under reduced pressure, thereby obtaining 285 g of a *Rubus coreanus* extract.

EXAMPLE 2

Preparation of Extract of Roasted Rubus coreanus 1 kg of dried *Rubus coreanus* was put in a glass container, roasted at 150° C. for 30 minutes, and then dried in the shade. The roasted and dried *Rubus coreanus* was added to 5 l of 80% ethanol aqueous solution, extracted three times under reflux, and then dipped at 15° C. for 1 day. Next, the dipped solution was filtered through filter cloth and centrifuged into residue and a filtrate, and the separated filtrate was concentrated under reduced pressure, thereby obtaining 250 g of an extract of roasted *Rubus coreanus*.

EXAMPLE 3

Preparation of Extract of Yellow Rice Wine-added Steamed Rubus coreanus 1 kg of dried *Rubus coreanus* was immersed in 300 ml of yellow rice wine (aged in a Korean traditional pottery in the shade and used in an amount of 20-30 wt % based on the weight of dried *Rubus coreanus*) for 1 hour so as to be wet with the yellow rice wine. The wet *Rubus coreanus* was steamed in a steam pot at 100~150° C. for 4 hours, and then dried in the shade. Next, the dried material was added to 5 l of 80% ethanol aqueous solution, extracted three times under reflux, and then dipped at 15° C. for 1 day. Next, the dipped solution was filtered through filter cloth and centrifuged into residue and a filtrate, and the separated filtrate was concentrated under reduced pressure, thereby obtaining 260 g of an extract of wine-added steamed *Rubus coreanus*.

EXAMPLE 4

Preparation of Extract of Brine-added Roasted Rubus coreanus 1 kg of dried *Rubus coreanus* was mixed well with 200 ml of brine (aged in a Korean traditional pottery in the shade and having a salt concentration of 8-10% and also used in an amount of 20-30 wt % based on the weight of dried *Rubus coreanus*) and allowed to stand for 1 hour in a closed state such that the brine was completely absorbed into the *Rubus coreanus*. Next, the brine-absorbed *Rubus coreanus* was put in a glass container, roasted at 150° C. for 30 minutes, and then dried in the shade. Then, the dried material was added to 5 l of 80% ethanol aqueous solution, extracted three times under reflux, and then dipped at 15° C. for 1 day. Next, the dipped solution was filtered through filter cloth and centrifuged into residue and a filtrate, and the separated filtrate was concentrated under reduced pressure, thereby obtaining 295 g of an extract of brine-added roasted *Rubus coreanus*.

TEST EXAMPLE 1

Inhibitory Effect on Membrane Fusion

The membrane fusion inhibitory effects of the *Rubus coreanus* extracts obtained in Examples 1 to 4 were tested. SNARE proteins, called SNAP25 (NMO11428), Syntaxin 1a (AF217197) and VAMP2 (NMO12663), respectively, were purified from *E. coli* Codon (+) RIL (Novagen) transformed by a biological technique. First, in order to make a liposome that is a vesicle particle labeled with a fluorescent substance, palmitoyloleoyl phosphatidylcholine (POPC) (62 mol %), dioleoyl phosphatidylserine (DOPS) (35 mol %), 1-oleoyl-2-[N-(7-nitro-2,1,3-benzoxadiazol-4-yl)amino]caproyl phosphatidylserine (NBD-PS) (1.5 mol %) and the fluorescent substance Rhodamin-PE (1.5 mol %) were mixed with each other to make 10 mM liposome (v-vesicle). In order to make a non-fluorescence-labeled liposome, DOPS and POPC were mixed with each other at a molar concentration of 35:65 to make 50 mM liposome (t-vesicle). In order to make a complex consisting of purified SNAP25 and Syntaxin 1a, purified SNAP25 and Syntaxin 1a were mixed with each other at a molar concentration of 1:1 and allowed to react at room temperature for 1 hour, and then mixed with the non-fluorescence-labeled liposome at a molar ratio of 100:1, and VAMP2 was combined with the fluorescent substance-containing liposome at a molar ratio of 50:1. Thereafter, the two kinds of liposome were dialyzed through a 10 kDa dialysis membrane with stirring at 4 for 24 hours, and then mixed with each other at a ratio of 3:7 (v-vesicle:t-vesicle). Then, to the mixture comprising SNAP-25, Syntaxin 1a and VAMP-2, each of methanol as a control and 40 µg/ml of each of the *Rubus coreanus* extracts of Examples 1 to 4 was added. Then, the fluorescence intensity of each of the mixtures was measured using a fluorescence intensity measurement device (Model: SpectraMax M2; manufactured by Molecular Device), and the measurement results are shown in FIG. 1. Because the fluorescence intensity in FIG. 1 means the membrane fusion between the SNARE proteins, lower fluorescence intensities show better effects on the inhibition of membrane fusion. The black circle indicates a pathway in which the control reaction progresses. As can be seen in FIG. 1, the *Rubus coreanus* extracts showed lower fluorescence intensities compared to the control, suggesting that these extracts had the effect of inhibiting the membrane fusion between the SNARE proteins. Particularly, the extract of wine-added, steamed *Rubus coreanus* (Example 3) had an excellent effect on the inhibition of membrane fusion compared to the other test groups.

The membrane fusion inhibition (%) of each of the *Rubus coreanus* extracts was calculated relative to 100 for the control, and the calculation results are shown in Table 1 below.

TABLE 1

| Membrane fusion inhibitory effects of *Rubus coreanu* extracts | | |
|---|---|---|
| Sample name | | Membrane fusion inhibition (%) |
| Control | | 100 |
| Example 1 | Extract of raw *Rubus coreanu* | 51 |
| Example 2 | Extract of roasted *Rubus coreanu* | 48 |
| Example 3 | Extract of wine-added, steamed *Rubus coreanu* | 0 |
| Example 4 | Extract of saline-added, roasted *Rubus coreanu* | 53 |

As can be seen in Table 1 above, the groups treated with the *Rubus coreanus* extracts showed excellent effects on the inhibition of membrane fusion compared to the control containing no *Rubus coreanus* extract. Also, the extract of wine-added, steamed *Rubus coreanus* (Example 3) had a significantly better effect on the inhibition of membrane fusion compared to the other *Rubus coreanus* extracts. This suggests that the *Rubus coreanus* extract of the present invention can exhibit an excellent effect of reducing skin wrinkles by effectively inhibiting the membrane fusion between SNARE proteins.

TEST EXAMPLE 2

Inhibitory Effect on the Release of a Neurotransmitter in PC12 Cells

PC12 cells were cultured in Ham's F12K medium, containing 10% fetal calf serum, 5% fetal bovine serum and antibiotics, in a collagen-coated plate (60 mm dish). For subculture, the medium was sucked from the culture plate, after which 2 ml of PBS was added to the culture plate, and the cells were isolated from the dish wall by pipetting and centrifuged at 1,000×g for 5 minutes. The cells were harvested, fresh medium was added thereto, and the cell pellets were dispersed by pipetting, added to a fresh culture plate and incubated in an incubator at 37 in the presence of 5% $CO_2$ gas. [$^3$H]-noradrenaline used in the test was purchased from Amersham. The medium was sucked from the PC12 cell culture plate, PBS was added to the culture plate, and the cells were detached from the plate wall, after which the number of the cells was counted with a hemacytometer. Then, the cells were dispersed and inoculated in fresh medium at a concentration of 2×10$^5$ cells/ml. After 24 hours, noradrenaline calibration buffer ([$^3$H]—NA, 1.5 μCi/ml) was added to the cells which were then incubated in a $CO_2$ gas incubator for 90 minutes. After incubation, the buffer was removed, after which the cells were washed three times with PBS. Then, the cells were inoculated in fresh medium, and 10 μg/ml of each of *Rubus coreanus* extracts of Examples 1 to 4 was added thereto and incubated for 30 minutes. As a positive control, Verapamil was used and the cells were treated with Verapamil in the same manner as treatment with the *Rubus coreanus* extract. After the medium has been removed, high-concentration $K^+$ buffer was added to the cells which were then incubated in a $CO_2$ gas incubator for 12 minutes. Then, the supernatant was collected and measured with a scintillation counter to determine whether the release of [$^3$H]-noradrenaline was inhibited. Whether the *Rubus coreanus* extracts inhibited the release of noradrenaline (dopamine derivative) in PC12 cells was determined as described above, and the ratio (%) of noradrenaline in each of the test groups was calculated relative to the high-concentration $K^+$ buffer. The results of the calculation are shown in FIG. 2.

Figure 2:
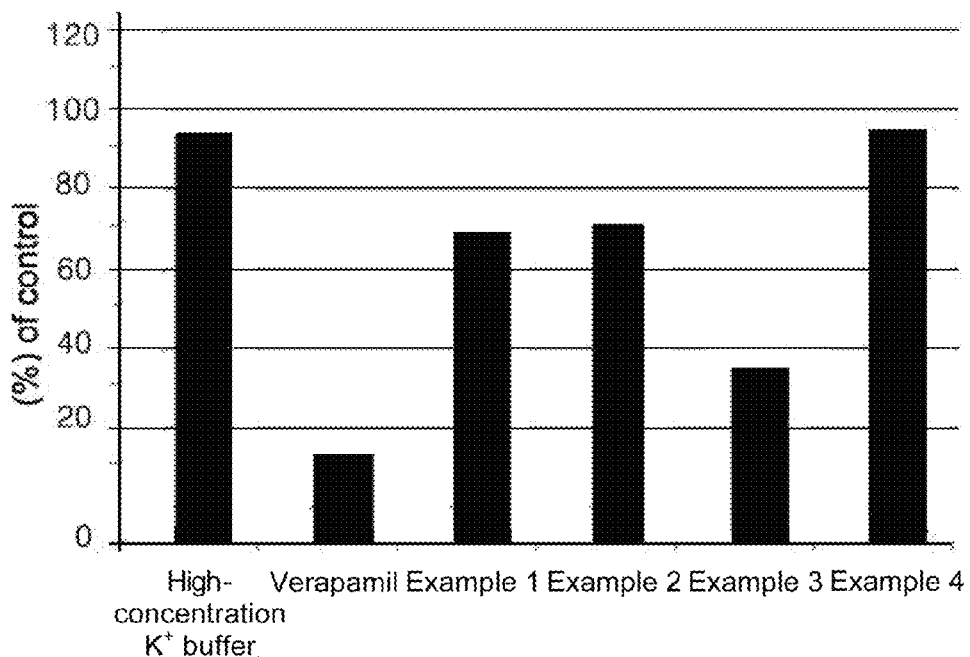
FIG. 2 is a graphic diagram showing the inhibitory effect of a *Rubus coreanus* extract according to the present invention on the release of a neurotransmitter in PC12 cells.

As can be seen in FIG. 2, the *Rubus coreanus* extracts other than the extract of saline-added roasted *Rubus coreanus*, used in the tests, effectively inhibited the release of the neurotransmitter, and the extract of wine-added steamed *Rubus coreanus* showed a relatively high inhibitory effect on the release of the neurotransmitter. This suggests that the *Rubus coreanus* extract of the present invention can exhibit an excellent effect of reducing skin wrinkles by inhibiting the release of a neurotransmitter.

Hereinafter, formulation examples of the composition according to the present invention will be described, but the scope of the present invention is not limited thereto.

FORMULATION EXAMPLE 1

Milk Lotion

A milk lotion containing an extract of wine-added steamed *Rubus coreanus* was prepared with the composition shown in Table 2 below.

TABLE 2

| Components | Contents (wt %) |
| --- | --- |
| Example 3 | 5.0 |
| Squalane | 5.0 |
| Beeswax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Caboxylvinyl polymer | 0.1 |
| Triethanolamine | 0.2 |
| Preservative, pigment and fragrance | q.s. |
| Purified water | balance |
| Total | 100 |

FORMULATION EXAMPLE 2

Skin Lotion

A skin lotion containing an extract of wine-added steamed *Rubus coreanus* was prepared with the composition shown in Table 3 below.

TABLE 3

| Components | Contents (wt %) |
| --- | --- |
| Example 3 | 5.0 |
| Glycerin | 3.0 |
| Butylene glycol | 2.0 |
| Propylene glycol | 2.0 |
| Caboxylvinyl polymer | 0.1 |
| PEG 12 nonylphenylether | 0.2 |
| Polysorbate 80 | 0.4 |
| Ethanol | 10.0 |
| Triethanolamine | 0.1 |
| Preservative, pigment and fragrance | q.s. |
| Purified water | balance |
| Total | 100 |

FORMULATION EXAMPLE 3

Nourishing Cream

A nourishing cream containing an extract of wine-added steamed *Rubus coreanus* was prepared with the composition shown in Table 4 below.

TABLE 4

| Components | Contents (wt %) |
| --- | --- |
| Example 3 | 5.0 |
| Polysorbate 60 | 1.5 |
| Sorbitan sesquioleate | 0.5 |
| PEG60 hydrogenated castor oil | 2.0 |
| Liquid paraffin | 10.0 |

TABLE 4-continued

| Components | Contents (wt %) |
|---|---|
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservative, pigment and fragrance | q.s. |
| Purified water | balance |
| Total | 100 |

FORMULATION EXAMPLE 4

Massage Cream

A massage cream containing an extract of wine-added steamed *Rubus coreanus* was prepared with the composition shown in Table 5 below.

TABLE 5

| Components | Contents (wt %) |
|---|---|
| Example 3 | 5.0 |
| Beeswax | 10.0 |
| Polysorbate 60 | 1.5 |
| Sorbitan sesquioleate | 0.8 |
| PEG60 hydrogenated castor oil | 2.0 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservative, pigment and fragrance | q.s. |
| Purified water | balance |
| Total | 100 |

FORMULATION EXAMPLE 4

Pack

A pack containing an extract of wine-added steamed *Rubus coreanus* was prepared with the composition shown in Table 6 below.

TABLE 6

| Components | Contents (wt %) |
|---|---|
| Example 3 | 5.0 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG 12 nonylphenylether | 0.3 |
| Polysorbate 60 | 0.3 |
| Preservative, pigment and fragrance | q.s. |
| Purified water | balance |
| Total | 100 |

TEST EXAMPLE 3

Skin Wrinkle-reducing Effect of a Cosmetic Composition Containing an Extract of Wine-added steamed *Rubus coreanus*

The cosmetic composition of Formulation Example 3 containing the extract of wine-added steamed *Rubus coreanus* was applied to the wrinkled eye rims of ten women over 40-year-old (average age: 44.5 years old) twice a day for 12 weeks in an amount of 0.2 g each time. Before application of the cosmetic composition ($T_0$) and 12 weeks after application of the cosmetic composition ($T_{12}$), the degree of reduction of skin wrinkles in the subjects ($\Delta W$) was evaluated objectively by experts and subjectively by the subjects on the basis of the 7-point criteria shown in Table 7 below. The results of the evaluation are shown in Tables 8 and 9.

TABLE 7

| Criteria for evaluation | |
|---|---|
| Criteria for evaluation of skin wrinkles | Score |
| Very severely increased | −3 |
| Increased | −2 |
| Slightly increased | −1 |
| Not changed | 0 |
| Slightly reduced | 1 |
| Reduced | 2 |
| Very reduced | 3 |

TABLE 8

| Objective evaluation by experts | | |
|---|---|---|
| | Degree of average reduction of wrinkles ($\Delta W$) | |
| Subjects | $T_0$ | $T_{12}$ |
| Subject 1 | 0 | 2 |
| Subject 2 | 0 | 2 |
| Subject 3 | 0 | 3 |
| Subject 4 | 0 | 1 |
| Subject 5 | 0 | 2 |
| Subject 6 | 0 | 2 |
| Subject 7 | 0 | 2 |
| Subject 8 | 0 | 3 |
| Subject 9 | 0 | 1 |
| Subject 10 | 0 | 3 |
| $\Delta W$ ($T_{12}$-$T_0$) | 2.1 | |

TABLE 9

| Subjective evaluation by subjects | | |
|---|---|---|
| | Degree of average reduction of wrinkles ($\Delta W$) | |
| Subjects | $T_0$ | $T_{12}$ |
| Subject 1 | 0 | 2 |
| Subject 2 | 0 | 3 |
| Subject 3 | 0 | 3 |
| Subject 4 | 0 | 2 |
| Subject 5 | 0 | 2 |
| Subject 6 | 0 | 2 |
| Subject 7 | 0 | 2 |
| Subject 8 | 0 | 2 |

TABLE 9-continued

Subjective evaluation by subjects

| Subjects | Degree of average reduction of wrinkles (ΔW) | |
| --- | --- | --- |
|  | $T_0$ | $T_{12}$ |
| Subject 9 | 0 | 1 |
| Subject 10 | 0 | 3 |
| ΔW ($T_{12}$-$T_0$) | 2.0 | |

As can be seen in Tables 8 and 9, when the cosmetic composition containing the extract of wine-added steamed *Rubus coreanus* according to the present invention was applied to the subjects for 12 weeks, the degrees of average reduction of skin wrinkles were shown to be 2.1 and 2.0 in the objective evaluation by the experts and the subjective evaluation by the subjects, respectively. This suggests that the cosmetic composition containing the *Rubus coreanus* extract according to the present invention has a significant effect on the reduction of skin wrinkles.

The invention claimed is:

1. A method of reducing skin wrinkles in a subject in need thereof comprising topically applying to affected skin a cosmetic composition comprising an effective amount of an ethanol extract of wine-added steamed *Rubus coreanus*,
   wherein the wine-added steamed *Rubus coreanus* is obtained by immersing *Rubus coreanus* in yellow rice wine and steaming at 100-150° C. for 3-6 hours, and wherein the ethanol extract of wine-added steamed *Rubus coreanus* is obtained by a method comprising the steps of:
   (1) combining the wine-added steamed *Rubus coreanus* with ethanol under reflux to provide an extract of wine-added steamed *Rubus coreanus*,
   (2) filtering the extract of wine-added steamed *Rubus coreanus* obtained in step (1) through filter cloth to form a filtered solution;
   (3) centrifuging the filtered solution obtained in step (2) into a residue and a filtrate; and
   (4) separating and concentrating the filtrate obtained in step (3) under reduced pressure to provide the ethanol extract of wine-added steamed *Rubus coreanus*.

2. The method of claim 1, wherein the cosmetic composition inhibits membrane fusion cells.

3. The method of claim 1, wherein the cosmetic composition inhibits release of a neurotransmitter in PC cells.

4. The method of claim 1, wherein the cosmetic composition inhibits formation of a SNARE (soluble N-ethylmaleimide-sensitive factor attachment protein receptor) complex.

* * * * *